: 4,370,327

Jan. 25, 1983

[54] CEPHALOSPORINS AND PHARMACEUTICAL COMPOSITIONS

[75] Inventors: Bernd Wetzel; Eberhard Woitun, both of Biberach; Wolfgang Reuter, Laupertshausen; Roland Maier, Biberach; Uwe Lechner, Ummendorf; Hanns Goeth, Biberach, all of Fed. Rep. of Germany

[73] Assignee: Boehringer Ingelheim GmbH, Ingelheim am Rhein, Fed. Rep. of Germany

[21] Appl. No.: 237,066

[22] Filed: Feb. 23, 1981

[30] Foreign Application Priority Data

Feb. 29, 1980 [DE] Fed. Rep. of Germany ....... 3007685

[51] Int. Cl.³ ................. C07D 501/22; C07D 501/36; C07D 501/46; C07D 501/57
[52] U.S. Cl. ..................................... 424/246; 544/21; 544/25; 544/27; 544/28
[58] Field of Search ....................... 544/25, 27, 21, 28, 544/24; 424/246

[56] References Cited

U.S. PATENT DOCUMENTS

| | | | |
|---|---|---|---|
| 4,093,801 | 6/1978 | Breuer et al. | 544/21 |
| 4,132,789 | 1/1979 | Nomura et al. | 544/25 |
| 4,258,184 | 3/1981 | Kai et al. | 544/28 |

FOREIGN PATENT DOCUMENTS

| | | |
|---|---|---|
| 2586 | 1/1982 | European Pat. Off. |
| 2556736 | 6/1976 | Fed. Rep. of Germany |
| 2924296 | 12/1979 | Fed. Rep. of Germany |
| 2927683 | 1/1980 | Fed. Rep. of Germany |
| 2928344 | 2/1981 | Fed. Rep. of Germany |

*Primary Examiner*—Mary C. Lee
*Attorney, Agent, or Firm*—Hammond & Littell, Weissenberger and Muserlian

[57] ABSTRACT

The invention is directed to cephalosporins of the formula

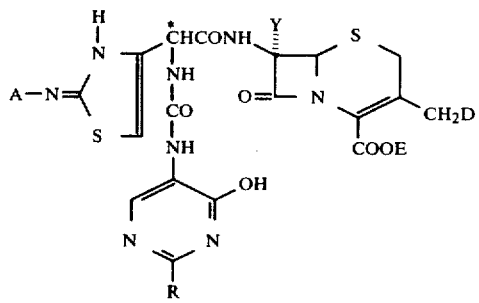

and the tautomers thereof, and, when E is a hydrogen atom, the pharmacologically acceptable salts thereof with inorganic or organic bases.

10 Claims, No Drawings

CEPHALOSPORINS AND PHARMACEUTICAL COMPOSITIONS

This invention relates to novel cephalosporins, to methods of preparing them, to pharmaceutical compositions containing them as active ingredients, and to methods of using said pharmaceutical compositions.

More particularly, the present invention relates to a novel class of cephalosporins represented by the formula

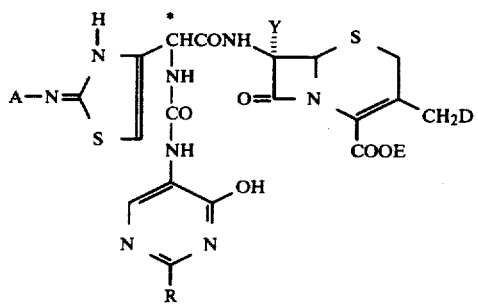

wherein

A is a hydrogen atom or a —COCH$_2$Cl, —COCH$_2$Br, —COOCH$_2$CCl$_3$, formyl, or trityl group;

Y, which is in the α-configuration, represents a hydrogen atom or a methoxy group;

D is a hydrogen atom, an acetoxy, aminocarbonyloxy, pyridinium, or aminocarbonylpyridinium group, or the group S-Het, where Het is tetrazol-5-yl, 1-methyl-tetrazol-5-yl, 1,3,4-thiadiazol-5-yl, 2-methyl-1,3,4-thiadiazol-5-yl, or 1,2,4-thiadiazol-5-yl group;

R represents a hydrogen atom; a cyclopropyl, hydroxyl, or methoxy group; a group of general formula —NHR$_1$, where R$_1$ represents a hydrogen atom, an aliphatic branched or unbranched hydrocarbon group of from 1 to 6 carbon atoms, optionally containing a double or triple bond, or a cycloalkyl group of from 3 to 6 carbon atoms; a group of general formula —NH—Z—X, wherein Z represents a linear or branched alkylene group of from 1 to 4 carbon atoms or a cycloalkyl group substituted by the substituent X and having from 3 to 6 carbon atoms, and X represents a hydroxyl, mercapto, cyano, aminocarbonyl, aminosulfonyl, acetyl, amino, methylamino, dimethylamino, formylamino, acetylamino, ureido, methylsulfonylamino, methoxy, ethoxy, acetoxy, methylmercapto, methylsulfinyl, methylsulfonyl, carboxyl, or methoxycarbonyl group; or a group of general formula

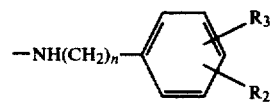

wherein n represents the integer 0 or 1 and R$_2$ and R$_3$, which may be the same or different, each represent a hydrogen or halogen atom or a hydroxyl, methyl, methoxy, acetylamino, aminocarbonylamino, alkylaminocarbonylamino, dialkylaminocarbonylamino, alkylsulfonylamino, alkylcarbonyl, alkylcarbonyloxy, aminocarbonyl, alkylaminocarbonyl, dialkylaminocarbonyl, nitro, cyano, methylmercapto, alkylsulfinyl, alkylsulfonyl, aminosulfonyl, alkylaminosulfonyl, or dialkylaminosulfonyl group, wherein the alkyl moieties may each comprise from 1 to 3 carbon atoms; and E is a hydrogen atom or a protective group which is easily removable in vitro or in vivo, such as those which have heretofore been used in the field of penicillins and cephalosporins, especially ester-forming groups which can be removed under mild conditions by hydrogenation or hydrolysis or other treatments, or esterforming groups which can easily be split off, in the living organism, or the possible tautomers thereof and, when E is a hydrogen, the non-toxic, pharmacologically acceptable salts thereof with inorganic or organic bases, such as the alkali-metal or alkaline earth metal salts, especially the sodium, potassium, magnesium, or calcium salts; the ammonium salts; or the organic amine salts, especially the triethylamine or dicyclohexylamine salts.

With respect to E, in vitro easily removable protective groups include, for example, benzyl, diphenylmethyl, trityl, tert.butyl, 2,2,2-trichloroethyl, and trimethylsilyl groups. Examples of protective groups easily removable in vivo include, for example, alkanoyloxyalkyl groups, preferably alkanoyloxyalkyl groups with from 1 to 4 carbon atoms in the alkanoyl group and from 1 to 3 carbon atoms in the alkylene group, such as, for example, an acetoxymethyl, propionyloxymethyl, 2-acetoxyethyl, or pivaloyloxymethyl group, and a phthalidyl group. Suitable protective groups also include alkali metal and alkaline earth metal ions, such as sodium or potassium ions.

When D represents a pyridinium or aminocarbonylpyridinium group, then the compounds of the invention have the general formula

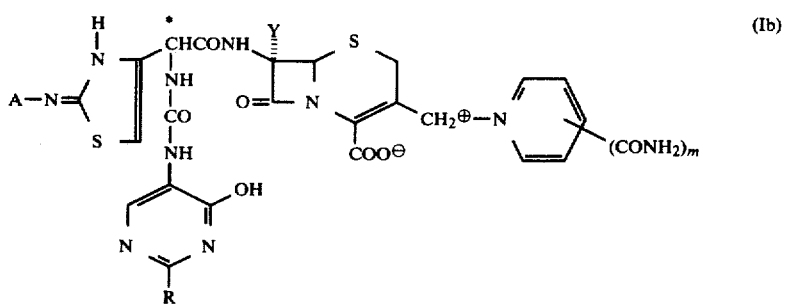

wherein m is 0 or 1.

The asterisk at the carbon atom in the compounds of the Formulas I and Ia indicates a center of asymmetry.

A preferred sub-genus is constituted by compounds of Formula I wherein
- A represents a hydrogen atom or a —COCH$_2$Cl group;
- Y represents a hydrogen atom or a methoxy group;
- D represents a hydrogen atom or an acetoxy, aminocarbonyloxy, pyridinium, or p-aminocarbonylpyridinium group or the group -SHet, wherein Het represents a 1-methyltetrazol-5-yl or 2-methyl-1,3,4-thiadiazol-5-yl group; and
- R and E are as defined above, and, when E is hydrogen, non-toxic, pharmacologically acceptable salts thereof.

An especially preferred sub-genus is constituted by compounds of Formula I, wherein
- A represents a hydrogen atom;
- Y represents a hydrogen atom or a methoxy group;
- D represents an acetoxy group or the group -SHet, where Het represents a 1-methyl-tetrazol-5-yl or 2-methyl-1,3,4-thiadiazol-5-yl group;
- E represents a hydrogen atom or a sodium ion; and
- R is a cyclopropyl group; a group of the general formula —NHR$_1$, wherein R$_1$ represents a methyl, ethyl, propyl, isopropyl, cyclopentyl, or cyclohexyl group; a group of general formula —N-H—Z—X, where (i) -NH-Z-represents a group of the formula

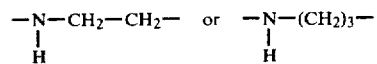

and X represents a hydroxyl, methoxy, aminocarbonyl, or aminosulfonyl group or (ii)

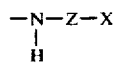

represents a 4'-hydroxycyclohexylamino group.

Another particularly preferred definition of R is a group of general formula

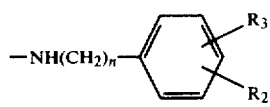

wherein n is an integer of 0 or 1 and R$_2$ and R$_3$, which may be the same or different, each represent a hydrogen or chlorine atom or a methyl, hydroxyl, acetylamino, methylsulfinyl, methylsulfonyl, aminocarbonyl, methylaminocarbonyl, aminosulfonyl, methylaminosulfonyl, dimethylaminosulfonyl, or aminocarbonylamino group. Even more preferred groups of Formula Ia include p-aminosulfonylanilino, p-methylsulfinylanilino, p-methylsulfonylanilino, m-hydroxy-p-aminosulfonylanilino, m,p-bis-(aminocarbonyl)-anilino, p-aminosulfonylbenzylamino, m,p-di-hydroxy-benzylamino, and p-hydroxybenzylamino groups.

The cephalosporin compounds of Formula I and the intermediate products described hereinafter may be present in a number of tautomeric forms (namely, with respect to the pyrimidine ring and the 2-amino-thiazolyl group). The particular choice of solvent used and the nature of the substituents A and R determine which of the following forms predominates:

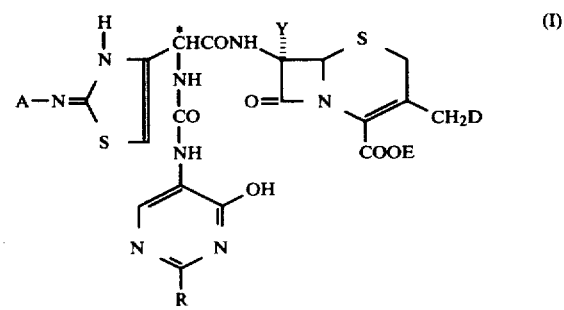

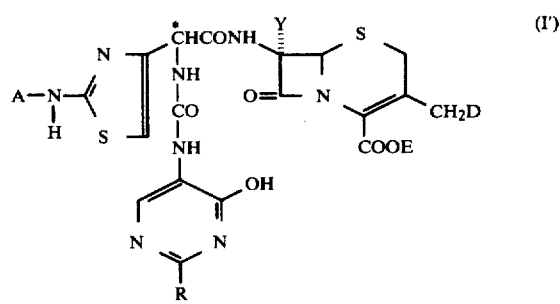

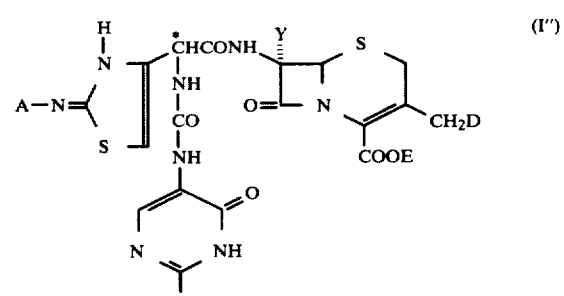

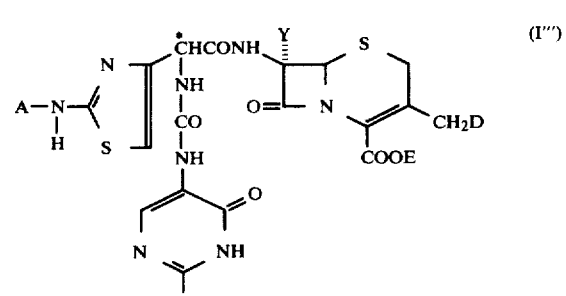

It should be understood that the compounds of Formula I specified at the beginning always include all the tautomers. In other words, reference to the compounds of Formula I can be considered a reference to the compounds of Formulas I, I', I'', and I''', unless otherwise indicated.

The compounds of Formula I may be present in the two possible R and S-configurations, with regard to the chiral center C, or as a mixture of these configurations.

The compounds of Formula I may be prepared by the following methods:

Method A

The compounds of general Formula I wherein D represents a hydrogen atom, an acetoxy group, an aminocarbonyloxy group, or a group of the formula -SHet, wherein Het has the above-mentioned meanings, may be prepared by reacting a 7-aminocephalosporanic acid derivative of the general formula

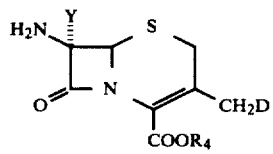
(II)

wherein
D represents a hydrogen atom, an acetoxy group, an aminocarbonyloxy group, or the group -SHet, and
R₄ represents a tert.butyl, benzyl, diphenylmethyl, trimethylsilyl, or 2,2,2-trichloroethyl group, but more particularly, a trimethylsilyl or diphenylmethyl group with ureidocarboxylic acids of the general formula

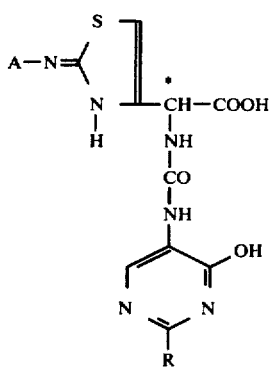
(III)

wherein A and R have the above meanings, or the salts or reactive derivatives thereof, to form an intermediate product of general formula

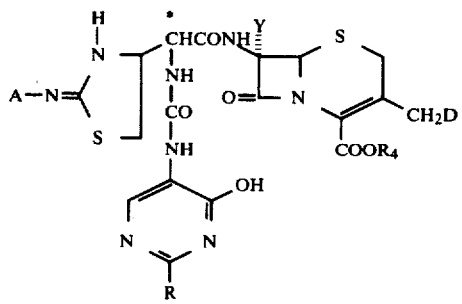
(IV)

Suitable reactive derivatives of the ureidocarboxylic acids of Formula III include, for example, the acid anhydrides thereof, such as, for example, those derived from chloroformates, for example, ethyl or isobutyl chloroformate, or the reactive esters thereof, such as the p-nitrophenyl ester or the N-hydroxy-succinimide ester, or the reactive amides thereof, such as N-carbonyl-imidazole, but also the acid halides thereof, such as the corresponding acid chloride or the acid azides.

In general, however, all the methods of bonding which are known in β-lactam chemistry can be used.

The ureidocarboxylic acid or a salt or reactive derivative thereof is reacted with the 7-aminocephalosporanic acid derivative in a solvent at temperatures between −40° C. and +40° C., optionally in the presence of a base. If, for example, an anhydride of the ureidocarboxylic acid, such as the anhydride with ethylchloroformate, is used, the reaction is carried out while cooling, for example, at from −10° C. to +10° C., in the presence of a solvent such as acetone, tetrahydrofuran, dimethylformamide, chloroform, dichloromethane, hexametapol, or a mixture of these solvents. If, for example, an N-hydroxysuccinimide ester of the ureidocarboxylic acid is reacted with a derivative of the compounds of Formula II, the reaction is preferably carried out at from 0° C. to 20° C. in the presence of a base such as triethylamine, in a solvent such as dimethylformamide, dichloromethane, dioxane, or a mixture of such solvents.

The reaction of a ureidocarboxylic acid of Formula III or a salt thereof with a compound of Formula II is advantageously carried out in the presence of a condensation agent, for instance in the presence of N,N'-dicyclohexylcarbodiimide. This direct acylation method is particularly preferred when A represents a hydrogen atom.

When R₄ represents diphenylmethyl, for example, the resulting intermediate product of general Formula IV is reacted with trifluoroacetic acid and anisole in known manner to form the compounds of general Formula I. If, for example, R₄ represents trimethylsilyl, the silyl protecting group may be separated in the usual way by aqueous hydrolysis.

Method B

The compounds of general Formula I wherein D has the meanings specified above with the exception of a pyridinium or aminocarbonyl-pyridinium group, are prepared by reacting 7-aminocephalosporanic acids of general formula

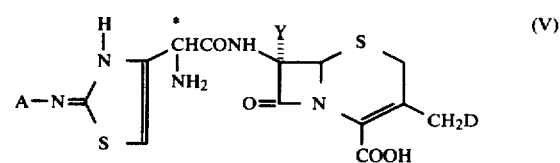
(V)

wherein
A and Y have the meanings previously defined and
D has the meanings previously defined with the exception of pyridinium or aminocarbonylpyridinium, or salts thereof with inorganic or organic acids, with a pyrimidine derivative of the formula

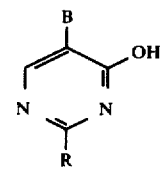
(VI)

wherein
R has the meanings previously defined, and
B is —NCO or a reactive derivative of —NHCOOH, such as, e.g., —NHCOCl, —NHCOBr, or

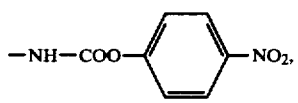

the group —NHCOCl being especially preferred.

Also, mixtures of such pyrimidine derivatives of Formula VI can be used, wherein B has partly the one and partly the other of the above-mentioned meanings, for instance, —NCO and —NHCOCl simultaneously.

The reaction is preferably carried out in any desired mixture of water with organic solvents which are miscible with water, such as ketones, for example, acetone; cyclic ethers, for example, tetrahydrofuran or dioxane; nitriles, for example, acetonitrile; formamides, for example, dimethylformamide; dimethylsulfoxide; or alcohols, for example, isopropanol, or in hexametapol. A mixture of tetrahydrofuran and water is particularly preferred. The pH of the reaction mixture is maintained in a pH range of from about 2.0 to 9.0, preferably from about 6.5 to 8.0, by the addition of bases or by using buffer solutions.

Method C

The compounds of general Formula I wherein E and A represent hydrogen and D represents the group —SHet or a pyridinium or aminocarbonyl-pyridinium group, may be prepared by reacting a compound of general formula

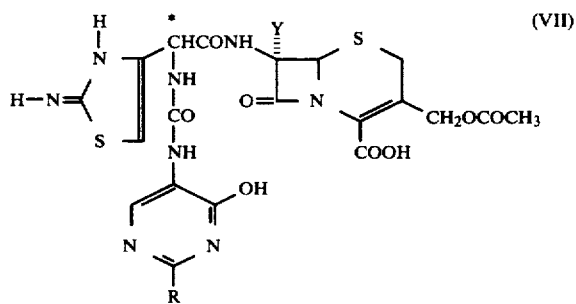

wherein R and Y have the meanings previously defined, with pyridine or aminocarbonylpyridine or with a compound of general formula Het-S-M   (VIII)

wherein Het has the above meanings and M represents a hydrogen atom or an alkali metal or an alkaline earth metal. For example, a compound of Formula VII is reacted with 1-methyl-5-mercapto-1,2,3,4-tetrazole in a solvent such as water, methanol, ethanol, acetone, methyl ethyl ketone, tetrahydrofuran, acetonitrile, ethyl acetate, dimethoxy-ethane, dimethylformamide, dimethyl sulfoxide, chloroform, or a mixture of any of these solvents. Preferably, a strongly polar solvent such as water or the like is used. In this case, the pH of the reaction solution is advantageously maintained in the range of from about 2 to 10, particularly from about 4 to 8. The desired pH-value can be adjusted by addition of a buffer solution, such as sodium phosphate. The reaction conditions are not subject to special restrictions. Normally, the reaction is carried out at a temperature in a range of from about 0° to 100° C., over a period of several hours.

Method D

A compound of general Formula I wherein Y is a methoxy group, can be obtained by reacting a compound of Formula I wherein Y represents a hydrogen atom in the presence of methanol with an alkali metal methylate of the formula $M^+OCH_3^-$, where $M^+$ represents an alkali metal, and then with a halogenating agent. For this purpose, a cephalosporin of Formula I wherein Y represents a hydrogen atom is dissolved or suspended in an inert solvent, such as tetrahydrofuran, dioxane, ethylene glycol dimethylether, methylene chloride, chloroform, dimethyl formamide, methanol, or the like or in a mixture of two of these solvents.

An alkali metal methylate together with methanol is added to the solution or suspension obtained. The resulting mixture is caused to react, and the reaction mixture is then reacted with a halogenating agent. In this reaction, methanol is used in excess, and the quantity of the alkali metal methylate is preferably from 2 to 8 equivalents per equivalent of cephalosporin. "Excess" means an amount of more than one equivalent per equivalent of cephalosporin. All reactions are carried out at temperatures of from about $-120°$ to $-10°$ C., preferably of from about $-100°$ to $-50°$ C. A reaction time of from 5 to 30 minutes is sufficient. The reaction is terminated by acidifying the reaction system.

The halogenating agent used in this process is generally known as source for positive halogen atoms, such as $Cl^+$, $Br^+$, or $I^+$. Examples of such halogenating agents are halogens, such as chlorine, bromine, etc.; N-haloimides, such as N-chlorosuccinimide, N-bromosuccinimide, and the like; N-haloamides, such as N-chloroacetamide, N-bromoacetamide, etc.; N-halosulfonamides, such as N-chlorobenzenesulfonamide, N-chloro-p-toluenesulfonamide, etc.; 1-halo-benzotriazoles; 1-halotriazines; organic hypohalites, such as tert.-butylhypochlorite, tert.butylhypoiodite, etc.; and halohydantoins, such as N,N-dibromohydantoin, etc. Tert.butylhypochlorite is preferred among these halogenating agents. The halogenating agent is used in a quantity sufficient to produce a quantity of positive halogen atoms equivalent to the amount of cephalosporin of Formula I.

Suitable acids for termination of the reaction are those which do not lead to solidification of the reaction mixture or to freezing of the reaction mixture into a heavy viscous mass when they are added to the cold reaction mixture. Suitable acids include, for example, 98% formic acid, glacial acetic acid, trichloroacetic acid, and methane sulfonic acid.

After interruption of the reaction, the excess halogenating agent is removed by treatment with a reducing agent, such as trialkyl phosphite, sodium thiosulfate, or the like.

The compounds of Formula I wherein A represents a group other than a hydrogen atom, prepared according to the above processes, can be treated in known manner to separate the imino protecting group. In this procedure, the compounds wherein A represents hydrogen, and which are the particularly preferred final compounds according to the invention, are obtained. For example, a compound of Formula I wherein A represents the chloroacetyl group and E represents a diphenylmethyl group is first treated with thiourea to separate the chloroacetyl group and is then treated in known manner with anisole and trifluoroacetic acid to separate the ester protecting group [cf. German Published Application (DE-OS) No. 2,924,296, incorporated herein by reference], or the ester protective group may be separated first and then the chloroacetyl protective group may be separated with sodium N-methyldithiocarbamate [cf. European Patent Publication (EP-OS) No. 2586, incorporated herein by reference].

The compounds of Formula I wherein E represents a sodium or potassium cation are prepared by reacting the corresponding free acid of the compounds of Formula I wherein E represents a hydrogen atom with the corresponding salt-forming ion. Suitable methods of doing this include, for example, reaction with sodium ethyl hexanoate conventionally used in the chemistry of penicillins and cephalosporins, and reaction with sodium hydrogen carbonate with subsequent freeze-drying.

Moreover, the cephalosporin antibiotics of Formula I wherein E represents a hydrogen in turn may be converted, in known manner, into the acyloxyalkyl esters, wherein E is, for example, a pivaloyloxymethyl radical

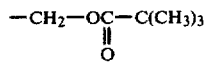

by reacting an alkali metal salt of the cephalosporin carboxylic acid, for example, a sodium or potassium salt, with a pivaloyloxymethyl halide of the formula

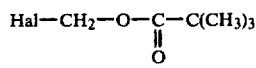

wherein Hal is chlorine, bromine or iodine.

Other suitable acyloxyalkyl halides include, for example, chloromethyl acetate, bromomethyl propionate, and 1-bromomethyl acetate.

When the corresponding starting compounds are used, it is possible to prepare the compounds of Formula I in the form of the racemates or in the form of the individual isomers. If the end product is obtained in the D,L-form, the pure D and L diastereoisomers may be prepared by preparative liquid chromatography (HPLC). The invention relates to the racemates and the isomers.

The ureidocarboxylic acid derivatives of Formula III are obtained by reacting the amino acid of the formula

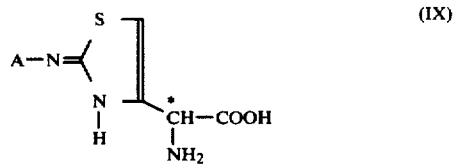

wherein A is as defined above, or the salts thereof with acids, such as with $CF_3COOH$, with a pyrimidine derivative of the Formula VI.

The reaction is carried out at temperatures of from about $-20°$ to $+40°$ C., preferably at from about $0°$ to $+20°$ C., in a solvent. Suitable solvents include, for example, mixtures of water and organic solvents miscible with water, such as acetone, tetrahydrofuran, dioxane, acetonitrile, dimethylformamide, ethanol, and dimethylsulfoxide. It may be necessary to use a hydrogen halide-binding agent. Suitable agents include, for example, trialkylamines, such as triethylamine, and inorganic bases such as dilute sodium hydroxide solution.

Derivatives of general Formula IX are known from the literature and are described, for example, in German Published Applications (DE-OS) Nos. 2,924,296 and 2,556,736, incorporated herein by reference.

The starting compounds of Formula VI can be obtained, for example, by reacting a corresponding 5-aminopyrimidine of the formula

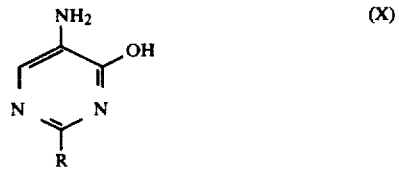

wherein R has the meanings previously defined, with phosgene. This reaction is preferably carried out in a solvent which does not contain hydroxyl groups, such as tetrahydrofuran, methylene chloride, chloroform, dimethoxyethane, or hexametapol, at temperatures of from about $-40°$ C. to $+60°$ C., preferably of from about $-10°$ to $+20°$ C. It is recommended to neutralize the hydrogen chloride released by the reaction with equimolar quantities of an inert organic base, such as triethylamine or pyridine. Also, pyridine in excess can be used as the solvent. If the particular aminopyrimidines of Formula X do not dissolve readily in one of the above-mentioned solvents, phosgenation can also be carried out in a heterogeneous system. In an especially preferred manner, the aminopyrimidines of Formula X can be converted by treatment with a silylating agent, such as hexamethyldisilazane, trimethyl chlorosilane/triethylamine, trimethylsilyl diethylamine, or N,O-bis-trimethylsilyl acetamide, into an aminopyrimidine which, in general, is very readily soluble in the above-mentioned solvents and which is, depending on the number of exchangeable hydrogen atoms present, mono- or polysilylated. After addition of phosgene, the aminopyrimidine reacts with the corresponding compound of Formula VI, the reaction preferably being carried out without the addition of a base.

Depending on the kind of solvent, the temperature, and the amount and nature of base which is optionally added, either mainly the corresponding isocyanate or carbamic acid halide, or a mixture of these two compounds, is obtained. Depending on the conditions, the isocyanate of Formula VI can also be present, either partly or wholly, as a dihydrooxazolo[5,4-d]pyrimidine of the general formula

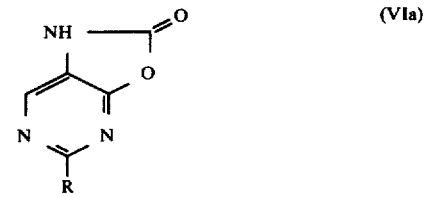

which is isomeric to the isocyanates. In accordance with the nature of the substituent R, the isocyanate of Formula VI may also be present as a mono- or polysilylated analog.

The starting products of Formula VI obtained by phosgenation or the mixtures or silyl derivatives thereof are generally readily soluble in the above-mentioned solvents and, after removal of the excess phosgene, can be reacted directly, without further purification, with the corresponding cephalosporin derivatives of Formula V. However, it is also possible to isolate the intermediate product of Formula VIa, to desilylate it with a protic solvent, for example, methanol or water, if required, to purify it, if necessary, on the basis of its solubility characteristics, and to react it in the manner described above.

Methods of synthesis for 2-substituted 5-amino-4-hydroxy-pyrimidines of Formula X are known from the literature and are described in German Published Application (DE-OS) No. 2,928,344, incorporated herein by reference.

The synthesis of starting products of Formula V is known from the literature. For this, a cephalosporin derivative of Formula II is reacted with an amino acid of Formula IX, protected at the amino group, under the conditions conventionally used in cephalosporin chemistry, and then the protective groups are separated as usual [cf. J. Antibiotics 1980, 1022 and German Published Application (DE-OS) No. 2,924,296].

The 7-amino-cephalosporanic acid derivatives of Formula II are known from the literature. The starting compounds of Formula VII can be prepared from the ureidocarboxylic acids of Formula III wherein A is hydrogen and the 7-amino-cephalosporanic acid derivatives of Formula II.

The compounds of the present invention, that is, those embraced by Formulas I, I', I'', and I''' and when E represents a hydrogen atom, the non-toxic, pharacologically acceptable salts thereof with inorganic or organic bases, have useful pharmacodynamic properties. More particularly, they exhibit very effective antibacterial activity in warm-blooded animals, such as mice. The compounds of the invention are very compatible, that is, they are well tolerated. Active substances according to the invention can therefore be used for the prophylaxis and chemotherapy of local and systemic infections in human and verterinary medicine.

Examples of diseases which can be prevented or cured by the compounds according to the invention include diseases of the respiratory tract, the pharyngeal cavity, and the urinary tract. The compounds are particularly effective against pharyngitis, pneumonia, peritonitis, pyelonephritis, otitis, cystitis, endocarditis, bronchitis, arthritis, and general systemic infections. Moreover, these compounds may also be used as substances for preserving inorganic or organic materials, especially organic materials such as polymers, lubricants, dyes, fibers, leather, paper, and wood, as well as foodstuffs. This is made possible by the fact that the compounds of Formula I are extremely effective both in vitro and in vivo against harmful microorganisms, particularly gram-positive and gram-negative bacteria and microorganisms resembling bacteria, and they are particularly distinguished by a broad range of activity.

Many local and/or systemic bacterial diseases can be treated and/or prevented by use of these cephalosporin derivatives of the present invention. Examples of such diseases include but are not limited to those caused by the following pathogenic microorganisms:
Micrococcaceae, such as staphylococci;
Lactobacteriaceae, such as streptococci;
Neisseriaceae, such as neisseria;
Corynebacteriaceae, such as corynebacteria;
Enterobacteriaeae, such as escherichiae bacteria of the coli group;
Klebsiella bacteria, such as pneumoniae;
Proteae bacteria of the proteus groups, such as proteus vulgaris;
Salmonella bacteria, such as thyphimurium;
Shigella bacteria, such as Shigella dysenteriae;
Pseudomonas bacteria, such as pseudomonas aeruginosa;
Aeromonas bacteria, such as aeromonas lique faciens;
Spirillaceae such as vibrio bacteria, such as vibrio cholerae;
Parvobacteriaeae or brucellaceae, such as pasteurella bacteria;
Brucella bacteria, such as brucella abortus;
Haemophilus bacteria, such as haemophilus influenzae;
Bordetella bacteria, such as bordetella pertussis;
Moraxella bacteria, such as moraxella lacunata;
Bacteroidaceae, such as bacteroides bacteria;
Fusiforme bacteria, such as fusobacterium fusiforme;
Sphaerophorus bacteria, such as sphaerophorus necrophorus;
Bacillaceae, such as aerobe spore formers, like bacillus anthracis;
Anaerobe spore formers chlostridia, such as chlostridium perfringens;
Spirochaetaceae, such as borrelia bacteria;
Treponema bacteria, such as treponema pallidum; and
Leptospira bacteria, such as leptospira interrogans.

The above list of pathogens is purely exemplary and is in no way restrictive.

Specific examples of compounds of the present invention, which exhibit broad spectrum antibacterial activity against gram-positive and gram-negative bacteria as well as against pseudomonas, include the following:

Sodium 7β-{D,L-α-[(2-cyclopropyl-4-hydroxy-5-pyrimidinyl)-ureido]-(2.3-dihydro-2-imino-4-thiazolyl)-acetamido}-3-[1-methyl-tetrazol-5-yl)-thiomethyl]-ceph-3-em-4-carboxylate Sodium 7β-{D,L-α-[(2-isoproylamino-4-hydroxy-5-pyrimidinyl)-ureido]-(2.3-dihydro-2-imino-4-thiazolyl)-acetamido}-3-[1-methyl-tetrazol-5-yl)-thiomethyl]-ceph-3-em-4-carboxylate Sodium 7β-{D,L-α-[(2-propylamino-4-hydroxy-5-pyrimidinyl)-ureido]-(2.3-dihydro-2-imino-4-thiazolyl)-acetamido}-3-[1-methyl-tetrazol-5-yl)-thiomethyl]-ceph-3-em-4-carboxylate Sodium 7β-{D,L-α-[(2-cyclopentylamino-4-hydroxy-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylate Sodium 7β-{D,L-α-[(2-(2'-hydroxyethylamino)-4-hydroxy-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylate Sodium 7β-{D,L-α-[(2-(3'-hydroxypropylamino)-4-hydroxy-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylate Sodium 7α-methoxy-7β-{D,L-α-[(2-(3'-hydroxypropylamino)-4-hydroxy-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate Sodium 7β-{D,L-α-[(2-(4'-hydroxycyclohexylamino)-4-hydroxy-5-pyrimidinyl)-ureido]-(2,3-dihydro-2- imino-4-thiazolyl)-acetamido}-3-[1-methyl-tetrazol-5-yl)-thiomethyl]-ceph-3-em-4-carboxylate Sodium 7α-methoxy-7β-{D,L-α-[(2-(4'-hydroxycyclohexylamino)-4-hydroxy-5-pyrimidinyl)-ureido]-(2,3-dihydro-2-imino-4-thiazolyl)-acetamido}-3-[1-methyl-tetrazol-5yl)-thio-methyl]-ceph-3-em-4-carboxylate Sodium 7β-{D,L-α-[(2-(2'-aminosulfonylethylamino)-4-hydroxy-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate Sodium 7β-{D,L-α-[(2-(3'-aminocarbonylpropylamino)-4-hydroxy-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate Sodium 7β-{D,L-α-[(2-(4'-hydroxycyclohexylamino)-4-hydroxy-5-pyrimidinyl)-ureido]-(2,3-dihydro-2-imino-4-thiazolyl)-acetamido}-3-acetoxymethyl-ceph-3-em-4-carboxylate Sodium 7β-{D,L-α-[(2-p-aminosulfonylanilino-4-hydroxy-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylate Sodium 7α-methoxy-7β-{D,L-α-[(2-p-aminosulfonylanilino-4-hydroxy-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylate Sodium 7β-{D,L-α-[(2-p-aminosulfonylanilino-4-hydroxy-5-pyrimidinyl)-ureido]-(2,3-dihydro-2-imino-4-thiazolyl)-acetamido}-3-acetoxymethyl-ceph-3-em-4-carboxylate Sodium 7β-{D,L-α-[(2-p-aminosulfonylanilino-4-hydroxy-5-pyrimidinyl)-ureido]-(2,3-dihydro-2-imino-4-thiazolyl)-acetamido}-3-[(2-methyl-1,3,4-thiadiazol-5-yl)-thiomethyl]-ceph-3-em-4-carboxylate Sodium 7β-{D,L-α-[(2-p-methylsulfinylanilino-4-hydroxy-5-pyrimidinyl)-ureido]-(2,3-dihydro-2-imino-4-thiazolyl)-acetamido}-3-[(1-methyltetrazol-5-yl)-thiomethyl]-ceph-3-em-4-carboxylate Sodium 7β-{D,L-α-[(2-p-methylsulfonylanilino-4-hydroxy-5-pyrimidinyl)-ureido]-(2,3-dihydro-2-imino-4-thiazolyl)-acetamido}-3-[(1-methyltetrazol-5-yl)-thiomethyl]-ceph-3-em-4-carboxylate Sodium 7β-{D,L-α-[2-(m-hydroxy-p-aminosulfonylanilino)-4-hydroxy-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate Sodium 7α-methoxy-7β-{D,L-α-[(2-(m-hydroxy-p-aminosulfonylanilino)-4-hydroxy-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate Sodium 7β-{D,L-α[(2-(m,p-bisaminocarbonylanilino)-4-hydroxy-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate Sodium 7β-{D,L-α-[(2-p-hydroxybenzylamino)-4-hydroxy-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate Sodium 7β-{D,L-α-[2-(m,p-dihydroxybenzylamino)-4-hydroxy-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylate Sodium 7β-{D,L-α-[2-(p-aminosulfonylbenzylamino)-4-hydroxy-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylate Sodium 7β-{D-α-[(2-p-aminosulfonylanilino-4-hydroxy-5-pyrimidinyl)-ureido]-(2,3-dihydro-2-imino-4-thiazolyl)-acetamido}-3-[-1-methyl-tetrazol-5-yl)-thiomethyl]-ceph-3-em-4-carboxylate Sodium 7β-{L-α-[(2-p-aminosulfonylanilino-4-hydroxy-5-pyrimidinyl)-ureido]-(2,3-dihydro-2-imino-4-thiazolyl)-acetamido}-3-[(1-methyltetrazol-5-yl)-thiomethyl]-ceph-3-em-4-carboxylate Sodium 7β-{D-α-[(2-p-hydroxybenzylamino)-4-hydroxy-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylate Sodium 7β-{L-α-[(2-p-hydroxybenzylamino)-4-hydroxy-5-pyrimidinyl)-ureido]-(2.3-dihydro-2-imino-4-thiazolyl)-acetamido}-3-[(1-methyl-tetrazol-5-yl)-thiomethyl]-ceph-3-em-4-carboxylate The effectiveness of the β-lactam antibiotics according to the invention can be demonstrated by way of example by the following tests:

1. In vitro tests

The tests were performed using the serial dilution test in the microtiter system. The effect of the text compounds on bacteriostasis was examined at the following concentrations: 128, 64, 32, 16, 8, 4, 2, 1, 0.5, 0.25, 0.12, 0.06, 0.03, and 0.015 μg/ml. The nutrient medium consisted of 10 gm of peptone, 8 g of meat extract oxoid, 3 g of sodium chloride, and 2 g of sec. sodium phosphate diluted with distilled water to 100 ml (pH 7.2–7.4). The age of the primary cultures was approximately 20 hours. The standardization of the bacteria suspension was effected using a photometer according to the method of Eppendorf (test tube φ 14 mm, filter 546 nm), using for comparison a barium sulfate suspension formed by the addition of 3.0 ml of 1% barium chloride solution to 97 ml of 1% sulfuric acid. After the standardization, the test pathogens were diluted further in a ratio of 1:1500 with a common salt solution.

Sixteen milligrams of a particular test compound were put into a 10 ml measuring flask, and the flask was subsequently filled to the mark with solvent. Further dilutions in the series were made with distilled water or the appropriate solvent.

The cavities of the microtiter plates were filled sequentially with 0.2 ml of nutrient medium, 0.01 ml of the appropriate test compound solution, and then 0.01 ml of the standardized bacteria suspension. The bacteria were incubated at 37° C. for from 18 to 20 hours. Control tests using only the solvent were carried out simultaneously.

The measurement was carried out macroscopically to determine the minimum inhibitory concentration (the lowest, still bacteriostatically effective concentration).

The following test organisms were used:
*Staphylococcus aureus* SG 511, *Escherichia coli* ATCC 11 775, *Pseudomonas aeruginosa Hamburgensis* and *Pseudomonas aeruginosa* Walter, *Serratia marcescens* ATCC 13 880, *Klebsiella pneumoniea* ATCC 10 031 and BC 6, *Proteus mirabilis* BC 17, *Proteus rettgeri* BC 7, *Enterobacter cloaceae* ATCC 13 047, and *E. coli* R+TEM (β-lactamase carrier), and *Klebsiella pneumoniae* 1082 E (β-lactamase carrier).

Representative compounds of the compounds of Formula I were tested. Those representative compounds comprised sodium salts of compounds of Formula I wherein R, D, and Y had the meanings set forth in the following table:

for Compounds A to G and the two comparison compounds:

TABLE 2

| Sub- | Minimum Inhibitory Concentration (μg/ml) | | | | | | | | | | | |
|---|---|---|---|---|---|---|---|---|---|---|---|---|
| | St. aureus SG 511 | E. coli ATCC 11775 | Pseud. aeru Hbg. | Pseud. aeru Walter | Klebs. pneum. ATCC 10031 | Klebs. pneum. BC 6 | Prot. mir. BC 17 | Prot. rettg. BC 17 | Enterob. cloacae ATCC 13047 | E. coli R + TEM | Serr. marcesc. ATCC 13880 | Klebs. pneum. 1082 E |
| Cefuroxime | 1 | 8 | >128 | >128 | 2 | 4 | 0.5 | 2 | 32 | 4 | 8 | — |
| Cefazoline | 0.06 | 4 | >128 | >128 | 1 | 2 | 4 | >128 | >128 | 4 | >128 | >128 |
| A | 1 | 0.03 | 32 | 32 | 0.03 | 0.06 | 0.03 | 0.12 | 0.5 | 0.5 | 0.25 | 32 |
| B | 1 | 0.06 | 32 | 32 | 0.12 | 0.06 | 0.06 | 0.12 | 0.25 | 0.5 | 0.25 | 16 |
| C | 2 | 0.06 | 32 | 32 | 0.25 | 0.12 | 0.06 | 0.25 | 0.5 | 1 | 0.25 | 32 |
| D | 2 | 0.06 | 16 | 16 | 0.06 | 0.06 | 0.12 | 0.12 | 0.25 | 1 | 0.25 | 32 |
| E | 0.5 | 0.03 | 16 | 8 | 0.06 | 0.06 | 0.12 | 0.12 | 0.25 | 1 | 0.12 | 32 |
| F | 1 | 0.06 | 16 | 16 | 0.12 | 0.12 | 0.25 | 0.25 | 0.5 | 2 | 0.5 | 64 |
| G | 0.5 | 0.03 | 16 | 8 | 0.06 | 0.03 | 0.03 | 0.06 | 0.12 | 0.5 | 0.12 | 16 |

TABLE 1

| Compound | R | D | Y |
|---|---|---|---|
| A | (cyclopropyl)- | N—N / \\ S—C C—N / \\ / N—N | H |
| | | CH₃ | |
| B | —NHC₃H₇ | (same thiadiazole ring with N—CH₃) | H |
| C | —NH(CH₂)₃OH | (same) | H |
| D | —NH—(cyclohexyl)—OH | (same) | H |
| E | —NH—(phenyl)—SO₂NH₂ | —OCOCH₃ | H |
| F | —NH—(phenyl)—SO₂NH₂ | (same thiadiazole) | H |
| G | —NH—CH₂—(phenyl)—OH | (same thiadiazole) | H |

Cefuroxime and Cephazolin, which are two well known and effective caphalosporins, were used as comparison compounds. The following table sets forth the minimum inhibitory concentrations (MIC) determined As can be seen from Table 2, the representative compounds of the invention, that is, Compounds A to G, are clearly superior to the comparison substances with regard to effectiveness against typical gram-negative hospital pathogens while also being active against gram-positive pathogens.

The acute toxicity was determined by oral and subcutaneous administration of the compounds of Tables 1 and 2 in increasing doses to white laboratory mice.

The $LD_{50}$ is the dose which results in the death of 50% of the animals within 8 days. All the substances had an $LD_{50}$ of over 4 g/kg when administered orally and an $LD_{50}$ of over 2 g/kg when administered subcutaneously, that is, no animals died at a dose of 2 g/kg. This means that the compounds are substantially non-toxic in practice.

A number of the compounds according to the invention were tested in vivo against experimental infections in mice. E. coli ATCC 11775 was used as the pathogenic bacteria. An intraperitoneal infection was produced with 0.2 ml of a bacterial suspension (with 5% mucin), which corresponds to about $1.4 \times 10^6$ E. coli bacteria per mouse. Female mice of the NMRI strain were divided up into groups of 10 animals. Two groups were untreated, and the other groups were treated with various doses of the cephalosporins according to the invention, administered subcutaneously, to determine the $ED_{50}$ (does at which 50% of the animals survived). One treatment was administered 1 hour after the infection.

In both cases, the observation period was 7 days. The results of these tests with representatives of the cephalosporins according to the invention are shown in the following table:

TABLE 3

| Compound | $ED_{50}$ (mg/kg) |
|---|---|
| A | 0.5 |
| D | <0.3 |
| E | 0.1–0.3 |
| G | <0.2 |
| Cefuroxime | >100 |
| Cefaperazone (T 1551) | 3.1 |

A further object of this invention is to provide pharmaceutical agents which can be used for the treatment of infectious diseases both in humans and in animals. For pharmaceutical purposes the compounds of the present invention are administered to warm-blooded animals perorally, parenterally, topically, or rectally as active ingredients in customary pharmaceutical compositions, that is, compositions consisting essentially of an inert pharmaceutical carrier and an effective amount of the active ingredient, such as tablets, coated tablets, capsules, granulates, suppositories, solutions, suspensions, emulsions, ointments, gels, creams, powders, and sprays. Advantageously the active ingredient or a mixture of the different active ingredients of Formula I may be administered to both humans and animals, in a dose of from about 5 to 500 mg/kg, preferably from about 10 to 200 mg/kg, of body weight at intervals of 24 hours, optionally administered in the form of several single doses. A single dose will preferably contain the active ingredient according to the invention in amounts of from about 1 to 250 mg/kg, preferably from about 10 to 60 mg/kg, of body weight. Depending on the type and body weight of the patient to be treated, on the type and severity of the disease, on the type of preparation, and on the route of administration as well as on the period or interval over which the administration takes place, it may, however, be necessary to deviate from the above dosages. Thus, it may be sufficient in some cases to administer less than the above-mentioned amount of active ingredient, while in other cases the above-mentioned amount of active ingredient must be exceeded. The optimum dosage and route of administration of the active ingredients which are necessary in each case can easily be determined by one skilled in the art.

When used as a feed additive, the new compounds may be administered in the usual concentrations and preparations together with the feed, or with feed preparations or with drinking water. They can thereby prevent, remedy, and/or cure infactions caused by gram-negative and gram-positive bacteria and can also promote growth and bring about an improvement in the utilization of the feed.

The following examples illustrate the present invention and will enable others skilled in the art to understand it more completely. It should be understood, however, that the invention is not limited solely to the particular examples given below.

EXAMPLES

Example 1

Sodium 7β-{-D,L-α-[(2-cyclopropylamino-4-hydroxy-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate (a) Three hundred and two milligrams (2 mmol) of 5-amino-2-cyclopropyl-4-hydroxy-pyrimidine were dissolved in a small amount of dry tetrahydrofuran and mixed with 0.27 ml of triethylamine. This solution was added dropwise at 0° C. to a solution of 200 mg of phosgene in 15 ml of dry tetrahydrofuran. The mixture was stirred for 5 minutes at room temperature and then concentrated by evaporation in vacuo to half its volume.

(b) An amount of 1.2 g (2 mmol) of 7β-[D,L-α-amino-(2,3-dihydro-2-imino-4-thiazolyl)-acetamido]-3-[(1-methyl-tetrazol-5-yl)-thiomethyl]-ceph-3-em-4-carboxylic acid trifluoroacetate [for the method of synthesis, see German Published Application (DE-OS) No. 2,924,296, page 35] was placed in a mixture of 30 ml of tetrahydrofuran and 20 ml of water, under cooling with ice. The pH of the mixture was carefully adjusted to from 8.5 to 9.0 with dilute sodium hydroxide solution. While being cooled with ice, the mixture prepared in step (a) was added dropwise thereto, and the pH was maintained at about 8.0 with dilute sodium hydroxide solution. After addition of the mixture was complete, the resultant mixture was stirred for 1 hour at 5° C. and for 1 hour at room temperature. It was then diluted with some water, and the tetrahydrofuran was evaporated off under water jet vacuum. The residual aqueous phase was extracted twice with ethyl acetate. The aqueous phase was then chromatographed on an ion exchange resin, Amberlite XAD-2, first water and then a mixture of water and methanol (75:25) being used as eluant. The fractions containing the product were freeze-dried.

Yield: 700 mg (53% of theory).

The free acid was suspended in water and dissolved by adding sodium hydrogen carbonate. The solution obtained was freeze-dried. A white powder was obtained.

IR spectrum: 1765, 1660, 1610 cm$^{-1}$;

NMR spectrum (DMSO+CD$_3$OD) signals at ppm: 1.25 (m,4H), 1.90 (m,1H), 3.50 (q,2H), 3.90 (s,3H), 4.20 (q,2H; partly covered by solvent), 4.95 (dd,1H), 5.3 (d,1H), 5.65 (dd,1H), 6.55 (d,1H), 8.55 (s,1H).

Example 2

Sodium 7β-{D,L-α-[(4-hydroxy-2-propylamino-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate The above cephalosporin was prepared using a procedure analogous to that of Example 1. The starting material was 170 mg (1 mmol) of 5-amino-4-hydroxy-2-propylamino-pyrimidine, which, after being reacted with 0.13 ml of triethylamine and 100 mg of phosgene in tetrahydrofuran, analogously to Example 1, was reacted with 600 mg (1 mmol) of the cephalosporin derivative used therein.

The product was worked up analogously to Example 1.

Yield: 305 mg of acid (46% of theory);

NMR spectrum (DMSO+CD$_3$OD) signals at ppm: 1.0 (t,3H), 1.6 (m,2H), 3.2 (t,2H), 3.65 (q,2H), 3.90 (s,3H), 4.25 (q,2H), 5.15 (dd,1H), 5.40 (d,1H), 5.65 (dd,1H), 6.60 (s,1H), 8.10 (s,1H).

Example 3

Sodium 7β-{D,L-α[(4-hydroxy-2-(3'-hydroxypropylamino)-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate Five hundred milligrams (2.7 mmol) of 5-amino-4-hydroxy-2-(3'-hydroxypropylamino)-pyrimidine were heated at 80° C. for 5 minutes with 3 ml of trimethyl-silyldiethylamine. The homogeneous mixture was evaporated to dryness in vacuo, and the solid product obtained was dissolved in 30 ml of dry tetrahydrofuran. This solution was added dropwise, under cooling with ice, to a solution of 275 mg of phosgene in 20 ml of tetrahydrofuran.

The reaction was continued using a procedure analogous to that of Example 1.

Yield: 1.14 g (61% of theory);

IR-spectrum: 1765, 1650, 1610 cm$^{-1}$;

NMR spectrum (DMSO+CD$_3$OD) signals at ppm: 1.85 (m,2H), 3.3 (m,2H), 3.45 (q,2H), 3.6 (m,2H), 3.95 (s,3H), 4.30 (q,2H), 4.95 (dd,1H), 5.3 (s,1H), 5.55 (dd,1H), 6.40 (d,1H), 8.15 (s,1H).

Example 4

Sodium 7β-{-D,L-α-[(2-p-aminosulfonylanilino-4-hydroxy-5-pyrimidinyl)-ureido]-(2,3-dihydro-2-imino-4-thiazolyl)-acetamido}-3-acetoxymethyl-ceph-3-em-4-carboxylate (a) The compound 7β-[D,L-α-amino-(2,3-dihydro-2-(chloroacetyl)-imino-4-thiazolyl)-acetamido]-3-acetoxymethyl-ceph-3-em-4-carboxylic acid trifluoroacetate was synthesized according to German Published Application (DE-OS) No. 2,924,296, page 24f.

(b) An amount of 1.4 g (5 mmol) of 5amino-2-p-aminosulfonylanilino-4-hydroxypyrimidine was silylated using the method set forth in Example 3 and reacted with phosgene. The reaction with the cephalosporin derivative was carried out according to the procedure of Example 1, as follows:

The aqueous phase was extracted twice at a pH of 8.0 with ethyl acetate and then adjusted to a pH of 3.0 with 2 N hydrochloric acid, under cooling with ice. The product precipitated was filtered off with suction and dried. An amount of 2.76 g (66% of theory) of crude cephalosporin derivative (protected by chloroacetyl at the imino group) was obtained.

The free acid obtained was dissolved in methanol, and a solution of diphenyldiazomethane in dioxane was added. The mixture was stirred for 3 hours at room temperature, and then the precipitate formed was filtered off with suction. An amount of 2.42 g of diphenylmethyl ester was obtained (74% of theory).

One gram of the diphenylmethyl ester thus obtained and 200 mg of thiourea were refluxed in 100 ml of a mixture of chloroform, methanol, and dioxane (2:1:1) for 2 hours. The solution obtained was evaporated to dryness in vacuo and the residue was mixed with water. Eight hundred milligrams of the diphenylmethyl ester of the above-designated compound were obtained.

These 800 mg were stirred in a mixture of 5 ml of methylene chloride, 8 ml of trifluoroacetic acid, and 4 ml of anisole for 30 minutes, under cooling with ice. The mixture was then evaporated to dryness in vacuo, and the residue was digested with ether. The solid product was filtered off with suction and converted into the sodium salt with sodium hydrogen carbonate.

IR spectrum: 1765, 1660, 1610 cm$^{-1}$;

NMR spectrum (DMSO+CD$_3$OD) signals at ppm: 2.05 (s,3H), 3.45 (q,2H), 4.75 (q,2H), 4.90 (dd,1H), 5.35 (s,1H), 5.65 (dd,1H), 6.55 (d,1H), 7.83 (dd,4H), 8.32 (s,1H).

Example 5

Sodium 7β-{D,L-α-[(2-p-aminosulfonylanilino-4-hydroxy-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate The compound was synthesized using a procedure analogous to that of Example 4. The starting materials were 1.0 g (3.57 mmol) of the pyrimidine mentioned in Example 4 and 2.0 g (3.6 mmol) of 7-[D,L-α-amino-(2,3-dihydro-2-(chloroacetyl)-imino-4-thiazolyl)-acetamido]-3-[(1-methyl-tetrazol-5-yl)-thiomethyl]-ceph-3-em-4-carboxylic acid.

Yield (after conversion into the diphenylmethyl ester, splitting off the chloroacetyl group and the ester group) of acid: 1.09 g (38.5% of theory);

IR spectrum: 1765, 1655, 1605 cm$^{-1}$ (sodium salt);

NMR spectrum (DMSO+CD$_3$OD) signals at ppm: 3.45 (q,2H), 3.95 (s,3H), 4.25 (q,2H), 4.90 (dd,1H), 5.30 (d,1H), 5.65 (dd,1H), 6.55 (d,1H), 7.80 (dd,4H), 8.33 (s,1H).

Example 6

Sodium 7β-{D,L-α[(4-hydroxy-2-p-methylaminosulfonylanilino-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate The above cephalosporin was prepared using a procedure analogous to that of Example 1. The starting material was 590 mg (2 mmol) of 5-amino-4-hydroxy-2-p-methylaminosulfonylanilino-pyrimidine, which, after being silylated and reacted with phosgene, was reacted with 1.2 g of the cephalosporin derivative of Example 1.

Yield: 680 mg of sodium salt (41% of theory);

IR spectrum: 1765, 1655, 1615 cm$^{-1}$;

NMR spectrum (DMSO+CD$_3$OD) signals at ppm: 2.35 (s,3H), 3.45 (q,2H), 3.90 (s,3H), 4.30 (q,2H), 4.90 (dd,1H), 5.30 (d,1H), 5.70 (dd,1H), 6.60 (d,1H), 7.8 (dd,4H), 8.30 (s,1H).

Example 7

(a)

D,L-α-[3-(4-Hydroxy-2-(4'-hydroxycyclohexylamino)-5-pyrimidinyl)-ureido]-(2,3-dihydro-2-imino-4-thiazolyl)-acetic acid (i) An amount of 1.73 g (0.01 mol) of D,L-α-amino-(2,3-dihydro-2-imino-4-thiazolyl)-acetic acid was dissolved with 10 ml of 1 N sodium hydroxide solution in a mixture of 60 ml of tetrahydrofuran and 20 ml of water.

(ii) An amount of 2.24 g (0.01 mol) of 5-amino-4-hydroxy-2-(4'-hydroxy-cyclohexylamino)-pyrimidine was suspended in 50 ml of dry tetrahydrofuran and refluxed with 6 ml of diethylamino-trimethylsilane until it dissolved. The mixture was evaporated to dryness in vacuo and dissolved again in 50 ml of tetrahydrofuran, and then the resulting solution was added dropwise, under cooling with ice, to a solution of 1.05 g of phosgene in 20 ml of dry tetrahydrofuran. This mixture was stirred for another 15 minutes under cooling with ice and then concentrated by evaporation in vacuo down to half its volume.

The solution was added dropwise to the solution prepared in step (i) above, under cooling with ice, the pH being maintained at 8.0. The cooling means was removed, and the mixture was stirred at room temperature for another hour. It was then diluted with 30 ml of water, and the tetrahydrofuran was removed in vacuo. The aqueous phase was extracted twice with ethyl acetate, and the aqueous phase was then adjusted to a pH of 3.8 with 2 N hydrochloric acid. The precipitate was removed by filtration with suction and dried in vacuo.

Yield: 2.35 g (56% of theory);

IR spectrum: 3300 (broad) 1640–1650, 1530 (broad signal), 1155 cm$^{-1}$;

NMR spectrum (DMSO+CD$_3$OD) signals at ppm: 1.35 (m,4H), 1.9 (m,4H), 3.55 (m,2H), 5.15 (s,1H), 6.5 (s,1H), 8.1 (s,1H).

(b) Sodium 7β-{D,L-α-[3-(4-hydroxy-2-(4'-hydroxycyclohex-ylamino)-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylate An amount of 2.08 g (0.005 mol) of the ureidocarboxylic acid from step (a) was dissolved in 50 ml of dry dimethylformamide. Then, 2.5 g of 7-amino-3-[(1-methyl-tetrazol-5-yl)-thiomethyl]-ceph-3-em-4-carboxylate, dissolved in 30 ml of methylene chloride, were added, followed by 1.15 g of dicyclohexylcarbodiimide, under cooling with ice.

The mixture is stirred overnight under cooling with ice and then evaporated to dryness in vacuo. The residue was stirred with 50 ml of methanol and then with 100 ml of methylene chloride. The solid product, after being filtered off with suction, was chromatographed on a silica gel column to remove any minor impurities (eluant: methylene chloride/methanol (5:1)).

The diphenylmethyl ester obtained was separated in the usual manner with 10 ml of trifluoroacetic acid and 4 ml of anisole, and the residue was converted into the sodium salt by use of sodium ethylhexanoate in dimethylformamide/methanol.

Yield: 1.90 g (31% of theory);

IR spectrum: 3340, 1765, 1660, 1540 cm$^{-1}$;

NMR spectrum (DMSO+CD$_3$OD) signals at ppm: 1.3 (m,4H), 1.9 (m,4H), 3.30–3.80 (m,4H), 3.95 (s,3H), 4.3 (m,2H), 5.05 (m,1H), 5.4 (s,1H), 5.65 (dd,1H), 6.50 (d,1H), 8.1 (s,1H).

Using this method, the following cephalosporins of general Formula I (wherein A = a hydrogen atom, E = -sodium ion, and Y = a hydrogen atom) were synthesized:

TABLE 4

| Example | R | D | IR Spectrum cm$^{-1}$ | NMR Spectrum (Signals at ppm) |
|---|---|---|---|---|
| 8 | —NH—⟨cyclohexyl⟩—OH | —OCOCH$_3$ | 1765, 1660 | 1.35 (m,4H), 1.9 (m,4H), 2.05 (s,3H), 3.5 (m,4H), 4.9 (m,2H), 5.05 (d,1H), 5.4 (s,1H), 5.65 (q,1H), 6.50 (d,1H), 8.15 (s,1H)* |
| 9 | —NH(CH$_2$)$_3$OH | —OCOCH$_3$ | 1760, 1650 | 1.85 (m,2H), 2.05 (s,3H), 3.3 (m,2H), 3.5–3.7 (m,4H), 4.85 (m,2H), 5.0 (dd,1H), 5.35 (s,1H), 5.60 (dd,1H), 6.40 (s,1H,broad), 8.15 (s,1H)* |
| 10 | —NH(CH$_2$)$_3$CONH$_2$ | 1-methyl-tetrazol-5-yl-thio | 1765, 1660 | 1.80 (m,2H), 2.3 (m,2H), 3.2–3.6 (m,4H), 3.95 (s,3H), 4.3 (q,2H), 5.0 (d,1H), 5.4 (s,1H), 5.65 (dd,1H), 6.50 (d,1H), 8.10 (s,1H)* |
| 11 | —NHCH$_2$—⟨phenyl⟩—OH | 1-methyl-tetrazol-5-yl-thio | 1760, 1650, 1610 | 3.55 (m,2H), 3.95 (s,3H), 4.35 (m,4H), 4.95 (t,1H), 5.30 (s,1H), 5.55 (dd,1H), 6.40 (d,1H), 6.7 (d,2H), 7.15 (d,2H), 8.05 (s,1H)* |
| 12 | —NHCH$_2$—⟨phenyl⟩(OH)(OH) | 1-methyl-tetrazol-5-yl-thio | 1760, 1650 | 3.60 (m,2H), 3.95 (s,3H), 4.25 (m,2H), 4.40 (s,broad, 2H), 4.95 (dd,1H), 5.35 s,1H), 5.55 (dd,1H), 6.40 (d,1H), 6.7 (m,2H), 7.1 (d,1H), 8.05 (s,1H)* |
| 13 | —NH—⟨phenyl⟩—SOCH$_3$ | 1-methyl-tetrazol-5-yl-thio | 1765, 1655, 1605 | 2.80 (s,3H), 3.55 (m,2H), 3.90 (s,3H), 4.3 (m,2H), 5.0 (dd,1H), 5.40 (s,1H), 5.60 (dd,1H), 6.45 (d,1H), 7.60 (q,4H), 8.33 (s,1H)* |
| 14 | —NHCH$_2$—⟨phenyl⟩—SO$_2$NH$_2$ | 1-methyl-tetrazol-5-yl-thio | 1725, 1655 | (Acid) 3.70 (m,2H), 3.95 (s,3H), 4.3 (m,2H), 4.65 (s,2H), 5.10 (m,1H), 5.40 (s,1H), 5.70 (dd,1H), 6.6 (d,1H), 7.55 (d,2H), 7.85 (d,2H), 8.10 (s,1H)** |

*DMSO + CD$_3$OD
**CDCl$_3$/D$_2$O

EXAMPLE 15

Sodium
7β-{D,L-α-[(2-p-aminosulfonylanilino-4-hydroxy-5-pyrimidinyl)-ureido]-(2,3-dihydro-2-imino-4-thiazolyl)-acetamido}-3-[1-methyl-tetrazol-5-yl)-thiomethyl]-ceph-3-em-4-carboxylate (a)

D,L-α-Amino(2,3-dihydro-2-(chloroacetyl)-imino-4-thiazolyl)-acetic acid trifluoroacetate An amount of 12.4 g (0.03 mol) of D,L-α-[(4-methoxyphenyl)-methoxycarbonyl]-amino-(2,3-dihydro-2-(chloroacetyl)-imino-4-thiazolyl)-acetic acid [for preparation, see German Published Application (DE-OS) No. 2,924,296] was stirred in 20 ml of methylene chloride together with 20 ml of trifluoroacetic acid and 10 ml of anisole for 15 minutes under cooling with ice. The mixture was then evaporated to dryness in vacuo, and the residue was digested with ether.

(b)

D,L-α-(2-p-Aminosulfonylanilino-4-hydroxy-5-pyrimidinyl)-ureido-(2,3-dihydro-2-(chloroacetyl)-imino-4-thiazol)-acetic acid An amount of 1.8 g (0.005 mol) of the compound from step (a) was dissolved with 1 N sodium hydroxide solution in a mixture of 50 ml of tetrahydrofuran and 20 ml of water. The reaction product of 1.4 g (0.005 mol) of 5-amino-2-p-aminosulfonylanilino-4-hydroxy-pyrimidine (with trimethylsilyldiethylamine and phosgene), dissolved in dry tetrahydrofuran, was added dropwise, under cooling with ice. The pH was maintained at 7.5. The mixture was stirred for 1 hour under cooling with ice and for 1 hour at room temperature. It was then diluted with a little water, and the tetrahydrofuran was evaporated off in vacuo. The aqueous phase was extracted twice with ethyl acetate and then acidified to a pH of 3.0. The product precipitated was filtered off with suction and dried.

Yield: 1.87 g (67.5% of theory).

(c) An amount of 1.1 (2 mmol) of the ureidocarboxylic acid thus obtained, in 25 ml of methylene chloride, was mixed with 210 mg of N-methylmorpholine and 225 mg of ethyl chloroformate at −20° C. The mixture was stirred for 10 minutes at −15° C., and then a solution of 1.00 g of diphenylmethyl 7-β-amino-3-[(1-methyl-tetrazol-5-yl)-thiomethyl]-ceph-3-em-4-carboxylate in dry methylene chloride was added. The resulting mixture was stirred for 1.5 hours at −10° C. and for 1 hour at room temperature. It was then evaporated to dryness. The residue was subjected to column chromatography on silica gel (eluant: methylene chloride/methanol (6:1)).

(d) One hundred and fifty milligrams of the diphenylmethyl ester thus obtained were dissolved in 20 ml of tetrahydrofuran and stirred with a solution of 20 mg of sodium N-methyl-dithiocarbamate in 3 ml of water for 5 hours at room temperature. The mixture was evaporated to dryness in vacuo. The residue was thoroughly mixed with 20 ml of methanol, filtered off with suction, and washed with ether. The resulting product was separated in the usual way with trifluoroacetic acid/anisole and converted into the sodium salts. The NMR and IR spectra were identical to those of the compound of Example 6.

The D,L compound thus obtained was separated into the D and L forms by preparative liquid chromatography (HPLC) using a 7 um reverse phase C8 column (Lichrosorb RP 8, made by E. Merck of Darmstadt). A mixture of 1000 parts water, 50 parts methanol, and 3 parts sodium hydrogen carbonate was used as the eluant. The eluate was monitored at 254 nm (UV radiation).

Using procedures analogous to that described above, the following cephalosporins were prepared:

TABLE 5

| Example | R | D | IR Spectrum cm$^{-1}$ | NMR Spectrum (DMSO + CD$_3$OD) (Signals at ppm) |
|---|---|---|---|---|
| 16 | −NH−⟨⟩−CONH$_2$ | (1-methyl-tetrazol-5-yl-thio) | 1760, 1645, 1605 | 3.60 (m,2H), 3.95 (s,3H), 4.3 (m,2H), 5.0 (m,1H), 5.45 (s,1H), 5.65 (dd,1H), 6.50 (d,1H), 7.7 (q,4H), 8.30 (s,1H) |
| 17 | −NH−⟨OH⟩−SO$_2$NH$_2$ | (1-methyl-tetrazol-5-yl-thio) | 1765, 1650 | 3.55 (m,2H), 3.95 (s,3H), 4.25 (m,2H), 5.0 (m,1H), 5.40 (s,1H), 5.60 (dd,1H), 6.45 (d,1H), 7.35 (m,1H), 7.75 (m,2H), 8.34 (s,1H) |

EXAMPLE 18

Sodium
7α-methoxy-7β-{D,L-α-[3-(4-hydroxy-2(4'-hydroxy-benzylamino-5-pyrimidinyl)-ureido]-2,3-dihydro-2-imino-4-thiazolyl)-acetamido}-3-[(1-methyl-tetrazol-5-yl)-thiomethyl]-ceph-3-em-4-carboxylate An amount of 1.8 g (0.002 mol) of the diphenylmethyl ester of the cephalosporin prepared in Example 11 was dissolved in 70 ml of dry tetrahydrofuran. At −70° C., a solution of 500 mg of lithium methoxide in 20 ml of dry methanol was added, and the mixture was stirred at this temperature for 3 minutes. Then, at −70° C., 300 mg of tert.butyl hypochlorite were added. The mixture was stirred at −70° C. for 45 minutes, and then 0.6 ml of glacial acetic acid and 150 mg of triethylphosphite were added. At room temperature, 100 ml of phosphate buffer (pH 7.0) were added, and the mixture was extracted 3 times with methylene chloride to which a little tetrahydrofuran had been added. The organic phase was separated, dried, and the solvent was eliminated in vacuo. The residue was chromatographed twice on a silica gel column (eluant: methanol/methylene chloride (1:6)). Two hundred and sixty milligrams of the desired diphenylmethyl ester (14% of theory) were obtained.

Separation to form the acid and conversion into the sodium salt was carried out as in Example 1.

IR spectrum: 1765, 1670, 1155 cm$^{-1}$;

NMR spectrum (DMSO+CH$_3$OD) signals at ppm: 3.45 (s,3H), 3.55 (m,2H), 3.95 (s,3H), 4.3 (m,2H), 4.55 (s,2H), 5.0 (s,1H), 5.45 (s,1H), 6.50 (d,1H), 6.7 (d,2H), 7.15 (d,2H), 8.05 (s,1H).

EXAMPLE 19

Sodium 7α-methoxy-7β-{D,L-α-[3-(4-hydroxy-2-(4′-hydroxycyclohexylamino)-5-pyrimidinyl)-ureido]-(2,3-dihydro-2-amino-4-thiazolyl)-acetamido}-2-[(1-methyl-tetrazol-5-yl)-thiomethyl]-ceph-3-em-4-carboxylate Five hundred and twenty milligrams of 7β-D,L-[2-amino-2-(2-aminothiazol-4-yl)acetamido]-7α-methoxy-3-(1-methyltetrazol-5-yl)thiomethyl-cephem-4-carboxylic acid [for method of synthesis, see German Published Application (DE-OS) No. 2,927,683] were suspended in a mixture of 10 ml of methanol and 10 ml of methylene chloride. Then, 0.30 ml of triethylamine were added to the suspension. At 0° C., the intermediate product prepared according to step (a) of Example 7 from aminopyrimidine (230 mg), trimethylsilyldiethylamine, and phosgene, suspended in tetrahydrofuran, was added to the resulting solution. The mixture was stirred at room temperature for 5 hours. The solvent was eliminated in vacuo. After 20 ml of water and 30 ml of ethyl acetate were added to the residue, it was adjusted to a pH of 7.0, and the ethyl acetate layer was separated off. The aqueous layer was acidified to a pH of 3.6 with 2 N hydrochloric acid. The precipitated product was filtered off with suction and converted into the sodium salt in the usual way.

Yield: 330 mg;

IR spectrum: 1765, 1660, 1610 cm$^{-1}$;

NMR spectrum (DMSO+CH$_3$OD) signals at ppm: 1.4 (m,4H), 1.8 (m,4H), 3.3–3.6 (m,4H), 3.45 (s,3H), 3.95 (s,3H), 4.3 (m,2H), 5.05 (s,1H), 5.40 (s,1H), 6.40 (d,1H), 8.10 (s,1H).

Using procedures analogous to that described above, the following 7α-methoxy cephalosporins were prepared:

TABLE 6

| Example | R | D | IR Spectrum cm$^{-1}$ | NMR Spectrum (DMSO + CD$_3$OD) (Signals at ppm) |
|---|---|---|---|---|
| 20 | Cyclopropyl | [2-methyl-1,3,4-thiadiazol-5-yl-thio structure, N-methyl] | 1760, 1650 | 1.25 (m,4H), 1.90 (m,1H), 3.45 (m,2H + s,3H), 3.95 (s,3H), 4.95 (s,1H), 5.35 (s,1H), 6.40 (d,1H), 8.50 (s,1H) |
| 21 | NH—⟨C$_6$H$_4$⟩—SO$_2$NH$_2$ (para) | [2-methyl-1,3,4-thiadiazol-5-yl-thio structure, N-methyl] | 1765, 1660 | 3.45 (s,3H), 3.60 (m,2H), 3.95 (s,3H), 4.35 (m,2H), 5.0 (s,1H), 5.45 (s,1H), 6.50 (d,1H), 7.7 (dd,4H), 8.32 (s,1H) |
| 22 | NH—⟨C$_6$H$_3$(OH)⟩—SO$_2$NH$_2$ | [2-methyl-1,3,4-thiadiazol-5-yl-thio structure, N-methyl] | 1765, 1660 | 3.40 (s,3H), 3.60 (m,2H), 3.95 (s,3H), 4.35 (m,2H), 5.0 (s,1H), 5.40 (s,1H), 6.45 (d,1H), 7.40 (m,1H), 7.80 (s,2H), 8.33 (s,1H) |

EXAMPLE 23

Sodium 7β-{D,L-α-[3-(2-(p-aminosulfonyl-anilino)-4-hydroxy-5-pyrimidinyl)-ureido]-(2,3-dihydro-2-imino-4-thiazolyl)-acetamido}-3-[(2-methyl-thiadiazol-5-yl)-thiomethyl]-ceph-3-em-4-carboxylate Six hundred milligrams of the cephalosporin prepared according to Example 4 were heated for 6 hours to 80° C. together with 180 mg of 2-methyl-5-mercapto-thiadiazole in 40 ml of nitromethane. The mixture was evaporated to dryness in vacuo, and the residue was dissolved in a mixture of acetone and ethyl acetate. Under cooling with ice, diphenyldiazomethane was added until the mixture remained violet in color, after which the mixture was evaporated to dryness. The residue was purified by column chromatograph (silica gel; eluant: methylene chloride/methanol (5:1)). The ester obtained was separated in the usual way, and the acid was converted into the sodium salt.

Yield: 285 mg;

IR spectrum: 1760, 1650, 1600 cm$^{-1}$;

NMR spectrum (DMSO+CD$_3$OD) signals at ppm: 2.75 (s,3H), 3.4 (m,2H), 3.95 (s,3H), 4,35 (m,2H), 4.94 (t,3H), 5.35 (s, broad, 1H), 5.60 (dd,1H), 6.40 (d,1H), 7.75 (q,4H), 8.32 (s,1H).

EXAMPLE 24

7β-{D,L-α-[(2-p-Aminosulfonylanilino-4-hydroxy-5-pyrimidinyl)-ureido]-(2,3-dihydro-2-imino-4-thiazolyl)-acetamido}-3-[(1-pyridino)-methyl]-ceph-3-em-4-carboxylic acid One gram of the sodium salt prepared according to Example 4, 140 mg of pyridine, 3 g of potassium thiocyanate, and 10 ml of water were heated at 50° C. for 8 hours. The pH was maintained at 6.0 to 6.5. About 20 ml of water were added, and the mixture was adjusted to a pH of 2.8 with dilute hydrochloric acid. The precipitated product was filtered off with suction and dried. This product was the thiocyanic acid salt of the desired compound. The free acid could have been obtained in the usual way using an ion exchanger column.

NMR spectrum (D₂O): 3.8 (m,2H), 5.05 (d,1H), 5.5 (s,1H), 5.7 M,2+1H), 6.55 (d,1H), 7.8 (q,2H), 8.2, 8.7, 9.0 (pyridinium protons).

The following examples illustrate a few pharmaceutical dosage units compositions comprising a compound of the present invention, namely, sodium 7β-{D,L-α-[-(2-p-aminosulfonylanilino-4-hydroxy-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylate, as an active ingredient. The parts are parts by weight, unless otherwise specified.

EXAMPLE 25

Tablets

The tablet composition was compounded from the following ingredients:

| Component | Amount |
|---|---|
| Active ingredient | 2.0 parts |
| Lactose | 5.0 parts |
| Potato starch | 1.8 parts |
| Magnesium stearate | 0.1 part |
| Talcum | 0.1 part |
| | Total: 9.0 parts |

Preparation

The ingredients were admixed in conventional manner, and the composition was compressed into 900 mg/tablets in a tablet-making machine. Each tablet was an oral dosage unit composition containing 200 mg of the active ingredient.

EXAMPLE 26

Coated tablets

Tablets prepared according to the procedure of Example 25 were then coated with a thin shell consisting essentially of a mixture of sugar, potato starch, talcum, and tragacanth. Each coated tablet comprised an oral dosage unit composition containing 200 mg of active ingredient.

EXAMPLE 27

Gelatin capsules

Five hundred milligram portions of active ingredient were filled into hard gelatin capsules of suitable size.

EXAMPLE 28

Injectable solution

Under aseptic conditions, 251 gm of active ingredient were dissolved in 2008 ml of distilled water suitable for injection. The solution was filtered through a Millipore filter (pore size: 0.22 μm), and 2.0 ml-portions of the filtrate were poured into 1000 vials (10 ml capacity). The contents of the vials were lyophilized, and the vials were then closed with a rubber stopper and sealed with an aluminum cap. According to this procedure, vials were obtained which each contained 250 mg of active ingredient (vial A).

Under likewise aseptic conditions, 2.0 ml-portions of a physiological saline solution were filled into ampules which were then sealed (ampule B).

Prior to injection, the contents of ampule B are added to the contents of vial A, whereby an injectable preparation suitable for intravenous administration is obtained.

EXAMPLE 29

Infusion solution

Distilled water for injection was poured into the vials A in amounts of 20 ml for two vials, and the resulting solution was dissolved in 250 ml of a 5% solution of glucose suitable for injection. In this way, solutions for continuous infusion were prepared.

Any one of the other compounds embraced by Formula I or, when E is a hydrogen, a non-toxic, pharmacologically acceptable salt thereof with an inorganic or organic base, may be substituted for the particular active ingredient employed in Examples 25 through 29. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the tautomeric formulas

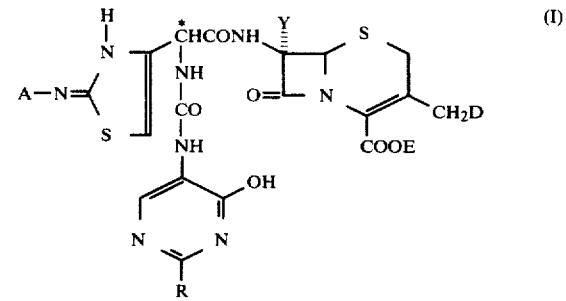

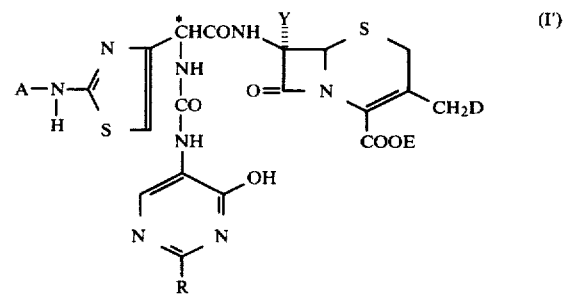

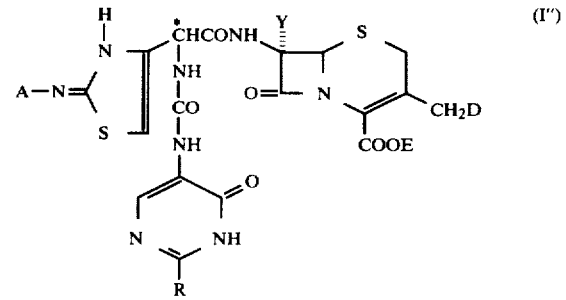

-continued and

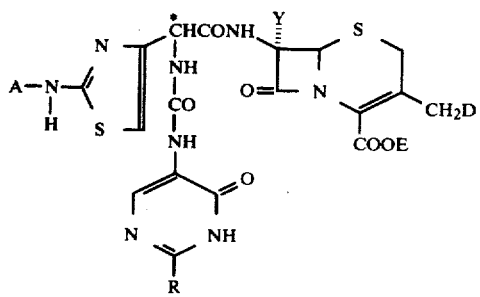

(I''')

wherein

A is a hydrogen atom or a —COCH$_2$Cl, —COCH$_2$Br, —COOCH$_2$CCl$_3$, formyl, or trityl group;

Y, which is in the α-configuration, represents a hydrogen atom or a methoxy group;

D is a hydrogen atom, an acetoxy, aminocarbonyloxy, pyridinium, or aminocarbonylpyridinium group, or the group S-Het, where Het is tetrazol-5-yl, 1-methyl-tetrazol-5-yl, 1,3,4-thiadiazol-5-yl, 2-methyl-1,3,4-thiadiazol-5-yl, or 1,2,4-thiadiazol-5-yl group;

R represents a hydrogen atom; or cyclopropyl, hydroxyl, or methoxy group; a group of general formula —NHR$_1$, where R$_1$ represents a hydrogen atom, an aliphatic branched or unbranched hydrocarbon group of from 1 to 6 carbon atoms, optionally containing a double or triple bond, or a cycloalkyl group of from 3 to 6 carbon atoms; a group of general formula —NH—Z—X, wherein Z represents a linear or branched alkylene group of from 1 to 4 carbon atoms or a cycloalkyl group substituted by the substituent X and having from 3 to 6 carbon atoms; and X represents a hydroxyl, mercapto, cyano, aminocarbonyl, aminosulfonyl, acetyl, amino, methylamino, dimethylamino, formylamino, acetylamino, ureido, methylsulfonylamino, methoxy, ethoxy, acetoxy, methylmercapto, methylsulfinyl, methylsulfonyl, carboxyl, or methoxycarbonyl group; or a group of general formula

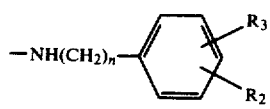 (Ia)

wherein n represents the integer 0 to 1 and R$_2$ and R$_3$, which may be the same or different, each represent a hydrogen or halogen atom or a hydroxyl, methyl, methoxy, acetylamino, aminocarbonylamino, alkylaminocarbonylamino, dialkylaminocarbonylamino, alkylsulfonylamino, alkylcarbonyl, alkylcarbonyloxy, aminocarbonyl, alkylaminocarbonyl, dialkylaminocarbonyl, nitro, cyano, methylmercapto, alkylsulfinyl, alkylsulfonyl, aminosulfonyl, alkylaminosulfonyl, or dialkylaminosulfonyl group, wherein the alkyl moieties may each comprise from 1 to 3 carbon atoms; and E is a hydrogen atom or a protective group which is easily removable in vitro or in vivo, or, when E is a hydrogen atom, a non-toxic, pharmacologically acceptable salt thereof with an inorganic or organic base.

2. A compound of claim 1, wherein

A represents a hydrogen atom or a —COCH$_2$Cl group;

Y represents a hydrogen atom or a methoxy group; and

D represents a hydrogen atom or an acetoxy, aminocarbonyloxy, pyridinium, or p-aminocarbonylpyridinium group or the group -SHet, wherein Het represents a 1-methyltetrazol-5-yl or 2-methyl-1,3,4-thiadiazol-5-yl group; and R and E are as defined in claim 1, or when E is a hydrogen atom, a pharmacologically acceptable salt thereof with an inorganic or organic base.

3. A compound of claim 1, wherein

A represents a hydrogen atom;

Y represents a hydrogen atom or a methoxy group;

D represents an acetoxy group or the group -SHet, where Het represents a 1-methyl-tetrazol-5-yl or 2-methyl-1,3,4-thiadiazol-5-yl group;

E represents a hydrogen atom or an alkali metal or alkaline earth metal ion; and R is a cyclopropyl group; a group of the general formula -NHR$_1$, wherein R$_1$ represents a methyl, ethyl, propyl, isopropyl, cyclopentyl, or cyclohexyl group; a group of general formula —NH—Z—X, wherein (i) —NH—Z— represents a group of the formula

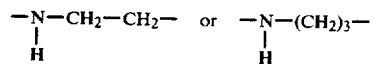

and X represents a hydroxyl, methoxy, aminocarbonyl, or aminosulfonyl group of (ii)

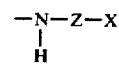

represents a 4'-hydroxycyclohexylamino group; or a group of general formula

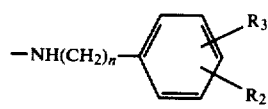 (Ia)

wherein n is an integer of 0 or 1 and R$_2$ and R$_3$, which may be the same or different, each represent a hydrogen or chlorine atom or a methyl, hydroxyl, acetylamino, methylsulfinyl, methylsulfonyl, aminocarbonyl, methylaminocarbonyl, aminosulfonyl, methylaminosulfonyl, dimethylaminosulfonyl, or aminocarbonylamino group, or, when E is a hydrogen atom, a pharmacologically acceptable salt thereof with an inorganic or organic base.

4. A compound of claim 3, wherein R represents a p-aminosulfonylanilino, p-methylsulfinylanilino, p-methylsulfonylanilino, m-hydroxy-p-aminosulfonylanilino, m,p-bis-(aminocarbonyl)-anilino, p- aminosulfonylbenzylamino, m,p-dihydroxy-benzylamino, or p-hydroxybenzylamino group.

5. A compound of claim 1, wherein E is a benzyl, diphenylmethyl, trityl, tert.butyl, 2,2,2-trichloroethyl, or trimethylsilyl group; an alkanoyloxyalkyl group with from 1 to 5 carbon atoms in the alkanoyl group and from 1 to 3 carbon atoms in the alkylene group; or a phthalidyl group.

6. A compound of claim 5, wherein E is an acetoxymethyl, propionyloxymethyl, 2-acetoxyethyl, or pivaloyloxymethyl group.

7. The compound of claim 1 which is 7-D,L-α-[(2-p-aminosulfonylanilino-4-hydroxy-5-pyrimidinyl)-ureido]-(2,3-dihydro-2-imino-4-thiazolyl)-acetamido-3-[(1-methyl-tetrazol-5-yl)-thiomethyl]-ceph-3-em-4-carboxylic acid or a pharmacologically acceptable salt thereof with an inorganic or organic base.

8. An antibiotic pharmaceutical composition consisting essentially of an inert pharmaceutical carrier and an effective antibiotic amount of a compound of claim 1.

9. The method of inhibiting the growth of or destroying pathogenic bacteria in a warm-blooded animal in need thereof, which comprises perorally, parenterally, rectally, or topically administering to said animal an effective antibiotic amount of a compound of claim 1.

10. A compound of claim 1, wherein E is a hydrogen atom; an alkali metal or alkaline earth metal ion; a benzyl, diphenylmethyl, trityl, tert.butyl, 2,2,2-trichloroethyl, or trimethylsilyl group; an alkanoyloxyalkyl group with from 1 to 5 carbon atoms in the alkanoyl group and from 1 to 3 carbon atoms in the alkyl group; or a phthalidyl group.

* * * * *